United States Patent [19]

Grychtol

[11] 3,932,446

[45] Jan. 13, 1976

[54] QUATERNIZED 6-DIETHYLAMINO-2-[BENZIMIDAZOLYL-(2)]BENZOFURAN

[75] Inventor: Klaus Grychtol, Bad Duerkheim, Germany

[73] Assignee: BASF Aktiengesellschaft, Ludwigshafen, Germany

[22] Filed: Sept. 6, 1973

[21] Appl. No.: 394,659

[30] Foreign Application Priority Data

Sept. 9, 1972 Germany............................ 2244371

[52] U.S. Cl.... 260/309.2; 252/301.2 R; 252/301.2 W; 427/158; 260/247.1 L; 260/247.5 EP; 260/247.7 G; 260/293.57; 260/293.58; 260/293.59; 260/293.6; 260/299; 260/304; 260/307 D; 260/346.2 R; 8/1 W; 8/178 R; 8/54.2

[51] Int. Cl.²...................................... C07D 235/14

[58] Field of Search.......................... 260/309.2, 299

[56] References Cited
UNITED STATES PATENTS 3,781,279 12/1973 Croanse et al............... 260/240 CA

OTHER PUBLICATIONS

Ciba "Central Patents Index" (8/72) No. 40511T Belgium Pat. No. 776,385.

*Primary Examiner*—Henry R. Jiles
*Assistant Examiner*—Robert W. Ramsuer
*Attorney, Agent, or Firm*—Johnston, Keil, Thompson & Shurtleff

[57] ABSTRACT

A benzofuran compound of the formula

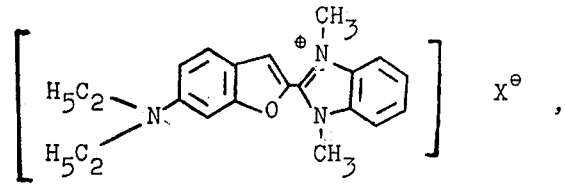

where $X^\ominus$ denotes $HSO_4^\ominus$, $CH_3SO_4^\ominus$, $Cl^\ominus$, $Br^\ominus$, ½ $2ZnCl_4^\ominus$ or $CH_3COO^\ominus$. The said compounds are dyes for synthetic textile material.

2 Claims, No Drawings

QUATERNIZED 6-DIETHYLAMINO-2-[BENZIMIDAZOLYL-(2)]BENZOFURAN

The invention relates to benzofuran compounds of the formula (I):

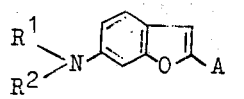 (I)

in which $R^1$ and $R^2$ are hydrogen, alkyl of one to six carbon atoms which may bear nonionic groups as substituents, phenyl or benzyl, and $R^1$ and $R^2$ may also be joined together to form a five-membered or six-membered ring, and A is one of the groups:

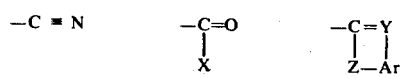

wherein X is —$OR^3$ or

Y is nitrogen quaternized by an epoxide or by benzyl or alkyl of one to four carbon atoms, Z is oxygen, sulfur, NH-, N-alkyl, N-cycloalkyl, N-aralkyl or N-aryl, Ar is unsubstituted or substituted o-phenylene or o-naphthylene, $R^3$ is hydrogen, alkyl, cycloalkyl, aralkyl or aryl and $R^4$ is hydrogen, alkyl, cycloalkyl, aralkyl, aryl or amino.

Benzofuran compounds of the formula (I) are colorless, yellow or red substances which exhibit strong fluorescence, particularly in organic solvents. In the case of the colored members of this class of substances the shade is dependent on pH. Because of this property they may be used in many fields, for example as optical brighteners, dyes or pigments or as dye precursors in copying processes.

Examples of nonionic groups which the alkyl groups $R^1$ and $R^2$ may bear as substituents are chloro, bromo, hydroxy or alkoxy of one to seven carbon atoms. Specific preferred radicals for $R^1$ and $R^2$ are methyl, ethyl, n-propyl, cyclohexyl, chloroethyl, hydroxyethyl, β-methoxyethyl, phenyl and benzyl of which methyl and ethyl are particularly preferred. When $R^1$ and $R^2$ are joined together to form a five-membered or six-membered ring, the morpholine, piperidine and pyrrolidine rings are preferred.

Examples of preferred alkyl, aralkyl and aryl radicals for $R^3$ and $R^4$ are: methyl, ethyl, propyl, phenyl and benzyl.

For compounds in which Z is N-alkyl, N-aralkyl or N-aryl the preferred alkyl radicals are methyl and ethyl, the preferred aryl radical is phenyl and the preferred aralkyl radical is benzyl.

Examples of substituents for the o-phenylene or o-naphthylene groups Ar are: chloro, hydroxy, methyl, ethyl, propyl, methoxy, ethoxy and β-methoxyethyl and one or more substituents are possible in the aromatic nucleus. In the case of the o-phenylene group a single substituent in the 5-position to the heteroatom Z is preferred.

When Y is nitrogen quaternized by an epoxide the epoxide radical may be for example hydroxyalkyl, β-phenylhydroxyalkyl or the radicals derived from epichlorohydrin or glycidamide.

Compounds of the formula:

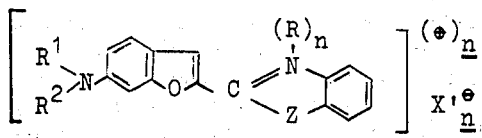

in which $X^-$ is an anion and R is alkyl of one to four carbon atoms or benzyl, n is zero or 1, $R^1$ and $R^2$ are methyl or ethyl and Z is NH, $NCH_3$, $NC_2H_5$, O or S are of particular industrial significance. The anion $X^-$ is preferably $HSO_4^-$, $CH_3SO_4^-$, $Cl^-$, $Br^-$, ½ $ZnCl_4^{--}$ or $CH_3COO^-$. Compounds illustrated by the following formulae are particularly suitable:

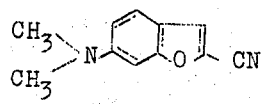

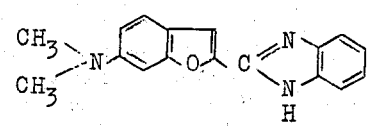

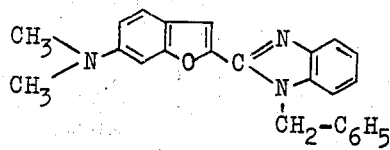

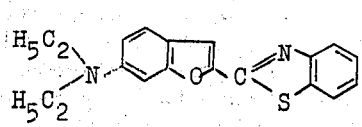

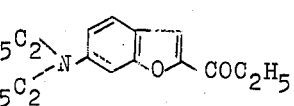

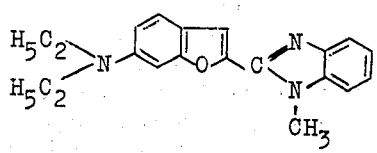

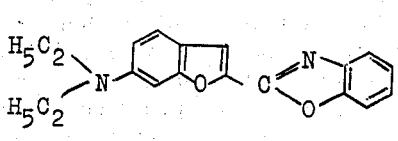

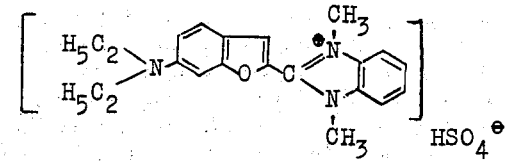

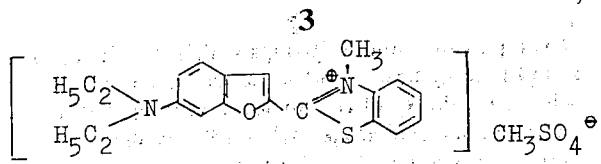

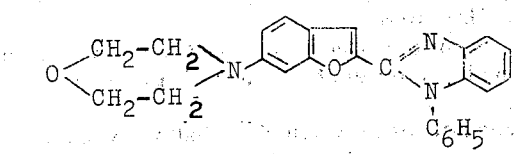

For the production of the benzofurans of the formula (I) the starting materials may be 4-aminosalicylaldehyde and its derivatives such as 4-dimethylaminosalicylaldehyde, 4-diethylaminosalicylaldehyde 4-dibutylaminosalicylaldehyde, 4-morpholinoalicyladehyde, 4-N-methyl-N-β-chloroethylaminosalicylaldehyde and 4-N-ethyl-N-phenylaminosalicylaldehyde and these may be condensed with acetic acid derivatives such as chloroacetic acid, ethyl chloroacetate, chloroacetamide and chloroacetonitrile or the corresponding bromine compounds by a conventional method, for example according to Bull. Soc. Chim. France 1971, pages 4329 to 4331, to form the phenoxyacetic acid compounds which by cyclization are converted into the benzofuran-2-carboxylic acid compounds of the formula (II):

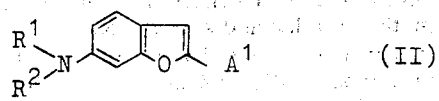

in which A¹ is

(When chloroacetonitrile or bromoacetonitrile are used it is possible to obtain the corresponding nitrile.) The condensation is conveniently carried out in solution in the presence of an acid-binding substance such as sodium hydroxide, potassium hydroxide, sodium carbonate, potassium carbonate, sodium hydrogen carbonate, sodium acetate, potassium acetate, sodium methylate, triethylamine or pyridine. Examples of suitable solvents are water; alcohols such as methanol, ethanol and ethylene glycol monomethyl ether; ketones such as acetone, methyl ethyl ketone and methyl isobutyl ketone; and carboxylic acid derivatives such as acetonitrile, dimethylformamide and N-methylpyrrolidone. Mixtures of solvents are also suitable. The phenoxyacetic acid compound obtained (either immediately or after previous isolation) is then converted conveniently in one of the abovementioned solvents in the presence of a base (for which purpose potassium hydroxide, potassium carbonate, potassium acetate and sodium methylate are particularly suitable) by cyclization into a benzofuran compound of the formula (II).

Heterocyclic substituted benzofurans of the formula (III):

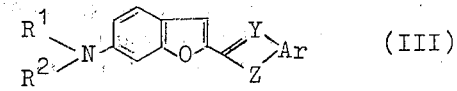

may be prepared from the compounds of the formula (II) by condensation by a conventional method with an o-substituted aniline such as o-phenylenediamine, o-aminophenol, o-aminothiophenol, 4-methyl-o-phenylenediamine, 4-chloro-o-phenylenediamine, 4-methyl-o-aminophenol, 4-methoxy-o-phenylenediamine, 4,5-dimethyl-o-phenylenediamine, N-methyl-o-phenylenediamine and 1,2-diaminonaphthalene. This condensation is conveniently carried out at a temperature in the range from 100° to 250°C and the components may be reacted with one another in substance or in solution and if desired in the presence of boric acid, phosphorus pentoxide, phosphoric acid or a polyphosphoric acid. High boiling point solvents such as nitrobenzene, trichlorobenzene, naphthalene, diphenyl or diphenyl oxide are particularly suitable as solvents. The reaction proceeds particularly advantageously in phosphoric acid or a polyphosphoric acid.

Quaternization of the nitrogen Y may be carried out by a conventional method, for example by reaction with an alkylating agent at a temperature of from 20° to 150°C; it is convenient to use the alkylating agent in excess and to carry out the reaction in water or an organic solvent such as cyclohexane, benzene, chlorobenzene, dimethylformamide, chloroform or acetonitrile and if desired in the presence of an acid-binding agent such as sodium hydrogen carbonate, sodium carbonate, potassium carbonate or magnesium oxide. Examples of preferred alkylating agents are dimethyl sulfate, diethyl sulfate, methyl p-toluenesulfonate, ethyl p-toluenesulfonate, benzyl bromide, methyl iodide, ethyl bromide, epichlorohydrin and styrene oxide.

The 6-dialkylaminobenzofuran-2-carboxylic acid derivatives according to the invention are colorless compounds which in organic solvents give strong blue to green fluorescence. The heterocyclic substituted benzofuran derivatives are colorless to yellow and give strong blue to green fluorescence in organic solvents. Because of the fluorescence properties the compounds are suitable for optical brightening of synthetic textile materials, particularly of synthetic polyamides and cellulose fibers. The colored compounds of the formula (I) may also be used as dyes for fibrous materials, preferably polyamides and modified cellulose.

The benzofuran compounds having quaternized nitrogen Y of the formula:

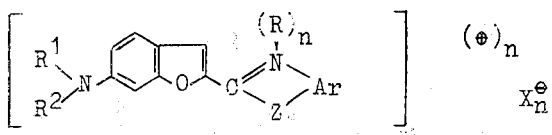

are particularly suitable for dyeing synthetic textile material, particularly of polyacrylonitrile and acid-modified polyesters, fluorescent yellow and red hues and for the production of print pastes for bright textile printing. Another preferred field is the production of daylight fluorescent pigments.

Solutions of benzimidazolyl-substituted benzofurans in solvents having little or no polarity such as hydrocarbons, chlorohydrocarbons and esters give intense yellow shades when acid substances are added. This reaction which is even caused by kaolin, zeolites, bentonite, silicic acid and phenolic condensation products renders the compounds suitable as dye precursors for pressure sensitive recording materials and particularly for copying papers.

Parts and percentages in the following illustrative Examples are by weight. Parts by volume bear the same relation to parts by weight as the liter to the kilogram.

EXAMPLE 1

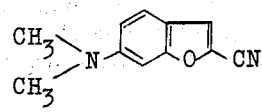

6-dimethylaminobenzofuran-2-carbonitrile 82 parts of 4-dimethylaminosalicylaldehyde is dissolved in 500 parts by volume of acetone, then 96 parts of potassium carbonate and 45 parts of chloroacetonitrile are added and the whole is boiled under reflux for 10 hours. After the solution has been filtered it is concentrated and the crystals deposited are recrystallized from benzene with the addition of animal charcoal. 36 parts of colorless crystals of 2-formyl-5-dimethylaminophenoxyacetonitrile is obtained with a melting point of 124° to 125°C.

15.3 parts of the nitrile is dissolved in 100 parts by volume of dimethylformamide and stirred with 10 parts of potassium carbonate for 15 hours at 70°C. The whole is then diluted with 1,000 parts of water, filtered by suction and the filter residue is dried. For further purification it is sublimed at 80°C and 1 mm and the sublimate is recrystallized from methylcyclohexane. The 6-dimethylaminobenzofuran-2-carbonitrile is obtained in the form of colorless crystals having a melting point of 70° to 71°C which dissolve in benzene with an intense blue-violet fluorescence.

Analysis: $C_{11}H_{10}N_2O$. calculated: C, 70.95; H, 5.41; N, 15.05. found: C, 70.7; H, 5.9; N, 14.9.

EXAMPLE 2

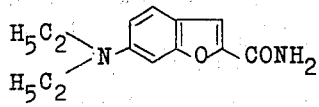

6-diethylaminobenzofuran-2-carboxamide

A mixture of 193 parts of 4-diethylaminosalicylaldehyde, 102 parts of chloroacetamide and 207 parts of powdered potassium carbonate in 800 parts by volume of methyl ethyl ketone is boiled under reflux for ten hours while stirring. The whole is filtered while hot and from the filtrate 137 parts of crystallized 2-formyl-5-diethylaminophenoxyacetamide is obtained having a melting point of 133°C.

When 4-dimethylaminosalicylaldehyde is used instead of 4-diethylaminosalicylaldehyde and the procedure is otherwise as described above, 2-formyl-5-dimethylaminophenoxyacetamide is obtained with a melting point of 147° to 148°C (yield: 56% of theory).

250 parts of 2-formyl-5-diethylaminophenoxyacetamide is dissolved in 1,000 parts by volume of dimethylformamide and 61.6 parts of powdered potassium hydroxide is added in portions, the temperature rising slightly. The whole is stirred overnight at ambient temperature and is worked up by pouring it into 2,000 parts of water. After the precipitate has been suction filtered it is washed until devoid of alkali, dried at 60°C and recrystallized from chlorobenzene. The yield is 199 parts of colorless needles having a melting point of 187° to 188°C.

Analysis: $C_{13}H_{16}N_2O_2$: calculated: C, 67.2; H, 6.9; N, 12.0. found: C, 67.4; H, 6.9; N, 12.0.

When 4-diethylaminosalicylaldehyde is reacted with chloroacetamide and potassium hydroxide in dimethylformamide at ambient temperature or with potassium carbonate instead of potassium hydroxide at refluxing temperature, the above benzofuran derivative is obtained in a similarly good yield.

When the equivalent amount of the dimethyl compound is used instead of 4-diethylaminosalicylaldehyde and the procedure is otherwise the same, 6-dimethylaminobenzofuran-2-carboxylic amide is obtained in a 68% yield. The melting point is 170° to 171°C.

Solutions of these benzofuran compounds in dioxane are colorless and exhibit a strong blue fluorescence in daylight. The compounds have good affinity for synthetic fibers, particularly polyamide and cellulose derivatives, and are therefore suitable for brigtening these substrates.

EXAMPLE 3

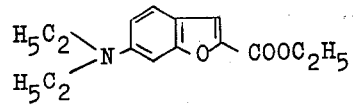

6-diethylaminobenzofuran-2-carboxylic ethyl ester

A solution of 193 parts of 3-diethylaminosalicylaldehyde and 200 parts of ethyl bromoacetate in 1,500 parts by volume of acetone has 193 parts of potassium carbonate added to it and it is then boiled for 15 hours. After cooling the whole is filtered and concentrated. By recrystallization from benzene with an addition of animal charcoal 255 parts of ethyl 2-formyl-5-diethylaminophenoxyacetate is obtained as colorless crystals having a melting point of 81° to 83°C.

Analysis: $C_{15}H_{21}NO_4$: calculated: C, 64.5; H, 7.6; N, 5.0; O, 22.9. found: C, 64.7; H, 7.6; N, 5.0; O, 22.9.

279 parts of this phenoxyacetic acid derivative in 400 parts by volume of dimethylformamide is boiled under reflux with 49 parts of potassium acetate for seven hours. After dilution with 600 parts of water it is shaken up with chloroform, dried and distilled 88 parts of 6-diethylaminobenzofuran-2-carboxylic acid ethyl ester is obtained which has a boiling point of 195° to 205°C at 4 to 6 mm and whose structure is confirmed by analysis and infrared and nuclear resonance spectra.

EXAMPLE 4

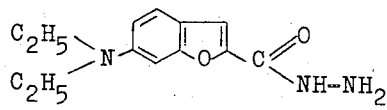

6-diethylaminobenzofuran-2-carboxylic hydrazide

Equimolar amounts of 6-diethylaminobenzofuran-2-carboxylic acid ethyl ester (Example 3) and hydrazine hydrate are boiled under reflux for three hours in solution in ethanol and after cooling to ambient temperature stirred for another twelve hours. The reaction mixture is poured into ice-water and the precipitate is suction filtered and washed with water. After recrystallization from alcohol the hydrazide is obtained in colorless crystals having a melting point of 127° to 129°C in a yield of 97%. (N: calculated 16.99, found 17.1). It dissolves in alcohol to give a colorless solution with a strong blue fluorescence.

EXAMPLE 5

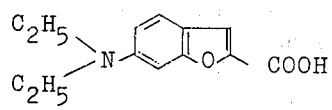

6-diethylaminobenzofuran 2-carboxylic acid

Hydrolysis of the amide of Example 2, the ester of Example 3 and the hydrazide of Example 4 with potassium hydroxide in water or an alcohol gives the 6-diethylaminobenzofuran-2-carboxylic acid. This decomposes at a temperature of more than 150°C with decarboxylation and formation of 6-diethylaminobenzofuran (boiling point 112° to 116°C at 3 to 4 mm). The alcoholic solutionn of the acid is colorless with a strong blue fluorescence.

EXAMPLE 6

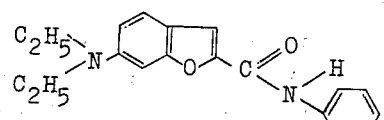

6-diethylaminobenzofuran-2-carboxylic anilide 5.8 parts of 6-diethylaminobenzofuran-2-carboxylic acid is dissolved in 50 parts of dioxane, then 0.3 part of dimethylformamide and 3 parts of thionyl chloride are added and the whole is boiled under reflux for 1 hour. After cooling 2.4 parts of aniline and 4 parts of pyridine are added and the whole is boiled under reflux for 3 hours, allowed to cool, diluted with 30 parts of water, stirred overnight at ambient temperature and suction filtered. After recrystallization from methylcyclohexane 3 parts of the carboxylic anilide is obtained having a melting point of 116° to 117°C.

EXAMPLE 7

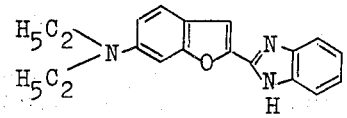

6-diethylamino-2-[benzimidazolyl-(2)]-benzofuran 23.2 parts of 6-diethylaminobenzofuran-2-carboxamide and 10.8 parts of o-phenylenediamine in 60 parts by volume of polyphosphoric acid are stirred for 2 hours at 100°C and then for 2 hours at 200°C. 400 parts of water is cautiously added at 140°C and the solution obtained is clarified with charcoal. A pH of from 5 to 6 is set up with 50% sodium acetate solution, and the precipitate formed is suction filtered, thoroughly washed and recrystallized from toluene. 21 parts of pale yellowish crystals are obtained with a melting point of from 243° to 244°C.

Analysis: $C_{19}H_{19}N_3O$: calculated: C, 74.7; H, 6.3; N, 13.8; O, 5.2 found: C, 74.8; H, 6.3; N, 14.2; O, 5.2.

The same compound is obtained by using the ethyl ester described in Example 3 (yield: 90%) instead of 6-diethylaminobenzofuran-2-carboxamide.

The compound dissolves in dioxane to give a colorless solution having a very strong blue fluorescence and is suitable for the optical brightening of synthetic fibrous materials.

When, the solution of the compound in toluene is enclosed in microcapsules and applied in this form to the surface of paper as a coating, a yellow color is obtained upon writing in contact with an acid acceptor layer.

The following benzofuran derivatives which have similar properties may be prepared by analogous methods:

EXAMPLE 8

From 4-chloro-o-phenylenediamine:
6-diethylamino-2-[5-chlorobenzimidazolyl-(2)]-benzofuran: melting point 232° to 233°C; color; yellowish.

EXAMPLE 9

From 4-methyl-o-phenylenediamine:
6-diethylamino-2-[5-methylbenzimidazolyl-(2)]-benzofuran: melting point: 240° to 241°C; color; pale yellow.

EXAMPLE 10

From 4,5-dimethyl-o-phenylenediamine:
6-diethylamino-2-[5,6-dimethylbenzimidazolyl-(2)]-benzofuran: melting point: 232° to 234°C; color: pale yellow.

EXAMPLE 11

From 4-methoxy-o-phenylenediamine:
6-diethylamino-2-[5-methoxybenzimidazolyl-(2)]-benzofuran: melting point: 203°C; color: pale yellow.

EXAMPLE 12

From N-methyl-o-phenylenediamine:

6-diethylamino-2-[1-methylbenzimidazolyl-(2)]-benzofuran: melting point: 238° to 239°C; color: pale yellow.

EXAMPLE 13

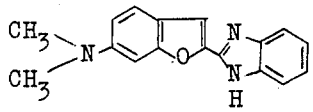

6-dimethylamino-2-[benzimidazolyl-(2)]-benzofuran 30.6 parts of 6-dimethylaminobenzofuran-2-carboxamide (see Example 2) and 16.2 parts of o-phenylenediamine are reacted as described in Example 7. The product is recrystallized from alcohol. 35 parts of yellowish needles are obtained which melt at 267° to 268°C.

EXAMPLE 14

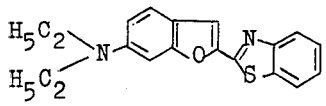

6-diethylamino-2-[benzothiazolyl-(2)]-benzofuran 23.2 parts of 6-diethylaminobenzofuran-2-carboxamide and 12.5 parts of o-aminothiophenol in 60 parts by volume of polyphosphoric acid are reacted as described in Example 7. After the product has been recrystallized from methylcyclohexane 22 parts of yellow crystals are isolated which melt at 125° to 126°C.

Analysis: calculated: N, 8.7; S, 9.9. found: N, 9.0; S, 9.7.

The compound dyes synthetic materials as for example polyamide and cellulose derivatives bright yellow hues.

EXAMPLE 15

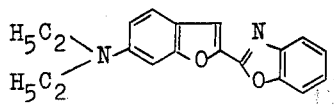

6-diethylamino-2-[benzoxazolyl-(2)]-benzofuran 23.6 parts of 6-diethylaminobenzofuran-2-carboxamide and 10.9 parts of o-aminophenol are reacted as described in Example 7. After recrystallization from methylcyclohexane with an addition of activated carbon the compound of the above formula is obtained in a yield of 62% in the form of yellowish crystals having a melting point of 120° to 122°C. The substance optically brightens synthetic fibers.

EXAMPLE 16

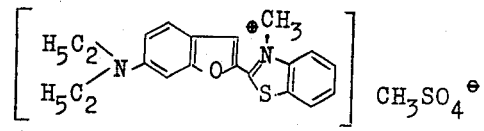

6.7 parts of the compound from Example 14 is boiled in 50 parts by volume of benzene with 3.8 parts of dimethyl sulfate for three hours, suction filtered and dried. 8.5 parts of red crystals are obtaind which melt at 178° to 180°C. The compound dyes polyacrylonitrile bright red hues.

EXAMPLE 17

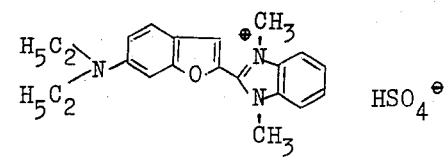

71 parts of 6-diethylamino-2-[benzimidazolyl-(2)]-benzofuran is made into a paste with 200 parts of water and stirred overnight with 80 parts of sodium hydrogen carbonate and 130 parts of dimethyl sulfate. After suction filtration 68 parts of a deep yellow substance is obtained which melts with decomposition at 193°C.

The compound, which has good solubility in water, colors polyacrylonitrile yellow hues having strong green fluorescence. It is suitable for the production of bright textile prints based on pigmented plastics and for the production of daylight fluorescent pigments.

I claim:

1. A benzofuran compound of the formula

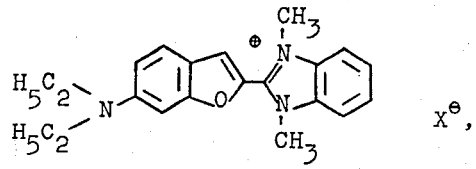

in which X⁻ is $HSO_4^-$, $CH_3SO_4^-$, Cl⁻, Br⁻, ½ $SnCl_4^{2-}$ or $CH_3COO^-$.

2. A compound as set forth in claim 1 wherein X⁻ is $HSO_4^-$.

* * * * *

UNITED STATES PATENT OFFICE
CERTIFICATE OF CORRECTION

PATENT NO. : 3,932,446
DATED : January 13, 1976
INVENTOR(S) : Klaus Grychtol

It is certified that error appears in the above-identified patent and that said Letters Patent are hereby corrected as shown below:

In the Abstract, delete " $1/2\ 2ZnCl_4^{\ominus}$ " and substitute -- $1/2\ ZnCl_4^{\ominus\ominus}$ --

In Column 10, Line 51 (Claim 1), delete " $1/2\ SNCl_4^{2\ \ominus}$ " and substitute -- $1/2\ ZnCl_4^{2\ \ominus}$ --

Signed and Sealed this

Fourth Day of January 1977

[SEAL]

Attest:

RUTH C. MASON
*Attesting Officer*

C. MARSHALL DANN
*Commissioner of Patents and Trademarks*